United States Patent [19]
Battault

[11] 3,977,026
[45] Aug. 31, 1976

[54] BONE PROSTHESIS MADE OF SINTERED ALUMINA

[75] Inventor: André Battault, Bazet, France
[73] Assignee: Ceraver, France
[22] Filed: May 29, 1975
[21] Appl. No.: 581,737

[30] Foreign Application Priority Data
May 29, 1974 France............................ 74.18588

[52] U.S. Cl................................. 3/1.91; 3/1.912; 128/92 C
[51] Int. Cl.² ........................................... A61F 1/24
[58] Field of Search ....................... 3/1, 1.9–1.913; 128/92 C, 92 CA

[56] References Cited
UNITED STATES PATENTS
2,668,531  2/1954  Haboush ..................... 128/92 CA
3,871,031  3/1975  Boutin .......................... 3/1

FOREIGN PATENTS OR APPLICATIONS
471,394  5/1952  Italy .............................. 128/92 CA Primary Examiner—Ronald L. Frinks
Attorney, Agent, or Firm—Craig & Antonelli

[57] ABSTRACT

Prosthesis device intended for replacing a bone joint, more particularly that of the hip, and comprising two parts which replace its active portions, the portion of each of the two parts on which the contact surface between these latter is formed being made of sintered alumina. One of the two parts has a spherical internal face forming a contact surface and an external face which is to be fixed into one of the bones of the joint, contained in a sphere and provided with grooves a part of which is arranged between cones whose apexes are on the axis and/or between cylinders having the same axis of symmetry as the external face. The surface provided for the bone cells to grow again is greater than that which would be provided by a part having grooves between planes perpendicular to the axis.

15 Claims, 2 Drawing Figures

BONE PROSTHESIS MADE OF SINTERED ALUMINA

The present invention concerns a prosthesis device intended to replace a joint and comprising two parts which replace the active portions of the joint.

It concerns, more particularly, a complete prosthesis device of the hip comprising a femoral part with a spherical head assembled on a metal or metallic alloy rod and with an acetabular part constituted by a concave hemisphere and provided with ribs or grooves on its convex face.

Generally, when the portion of at least one part coming in contact with the osseous portion on which it is to be fixed, is provided with ribs of grooves; these latter promote the bone cells to grow again extensively, this ensuring good natural fixing of the part in the bone, without the use of cement, this fixing being all the better as the surface of grooves offered for the bone to grow again is greater.

An object of the present invention is to increase the number and the surface of the grooves for a given external surface of the part coming in contact with the osseous portion to which it is to be fixed and to ensure thus a more solid natural fixing of the part to the osseous portion.

The prosthesis device according to the invention is characterized in that one of its two parts has a spherical internal face forming a contact surface and an external face intended to be fixed in one of the bones of the joint, contained in a sphere in relation to an axis of which it is symmetrical, and provided with grooves at least a part of which is arranged between two cones whose apexes are on the said axis and/or between cylinders having the same axis of symmetry as the said external face.

It comprises, moreover, preferably, at least one of the following characteristics:

The cones have their apex near the centre of the sphere in which the external face is contained;

The generatrixes of the cones form an angle of about 45° with the axis of the part;

The grooves of the portion of the external face of the said part which is the closest to the intersection of the axis with the enveloping sphere are arranged between cylinders which are coaxial to the said external face, those of the portion of that external face which is the furthest from the intersection of the axis with the enveloping sphere are arranged between planes perpendicular to that axis and those of the intermediate portion of the external face are arranged between cones whose apexes are on the said axis;

At least the portion of each of the two parts on which the contact surface between these latter and the external face of the said first part is formed is made of sintered alumina.

Acetabular parts of a hip prosthesis, the one known, the other according to the present improvement, are described hereinafter by way of example and with reference to the figures of the accompanying drawing.

Figure 1:
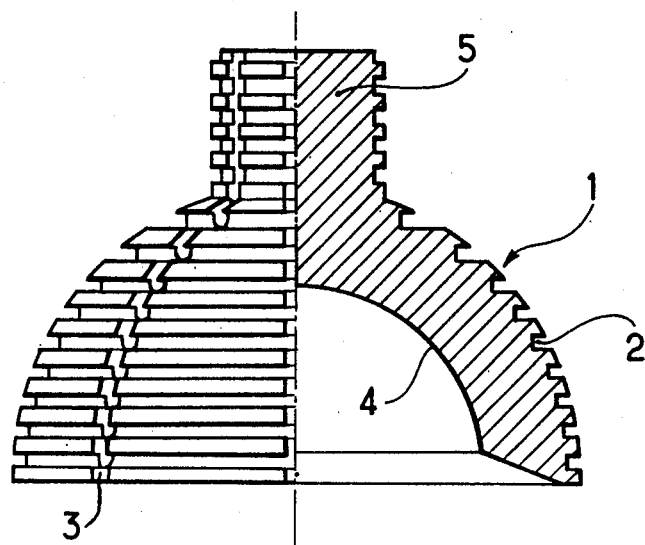
FIG. 1 shows a known acetabular part partly in an elevation view and partly in an axial cross-section view.

The acetabular part in FIG. 1 has a substantially hemispherical shape and comprises a concave face 4 which is ground and lapped. This face is that which ensures the gliding contact between the two parts of the joint. The convex face 1, which is used for fixing on the osseous substance, comprises grooves 2 and 3, arranged respectively along longitudinal and latitudinal lines of the enveloping sphere.

Moreover, that part comprises an axial cylindrical fixing pin 5, placed on the top of the half-sphere. That pin improves the mechanical connection between the part and that osseous portion to which it is fixed. That pin is also provided with grooves perpendicular to its axis and with grooves situated in diametrical planes.

By way of an indication, the grooves 2 and 3 can have a width of 1.2 mm and a depth of 1 mm.

The grooves arranged along the longitudinal lines such as 2 are 9 in number on the hemi-spherical surface and the grooves arranged on the latitudinal lines such as 3 are 8 in number.

Figure 2:
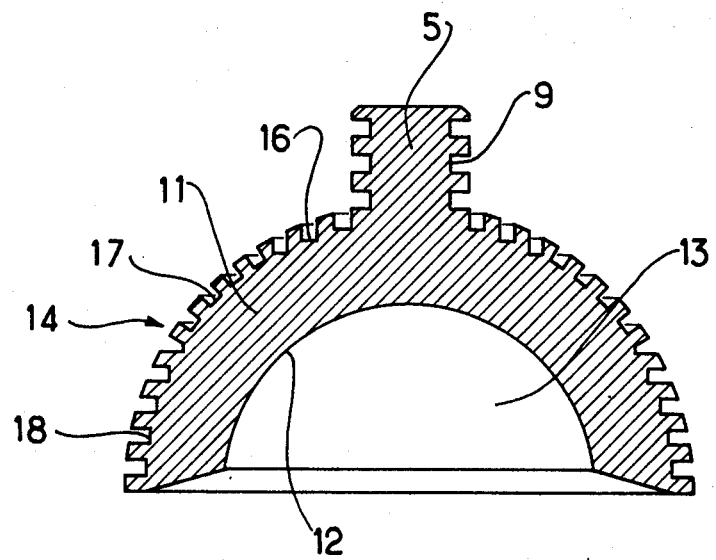
FIG. 2 shows an acetabular part according to the present improvement, in an axial cross-section view.

In FIG. 2, the acetabular part 11, which is substantially hemi-spherical and has an outside diameter of 48 mm, comprises a lapped internal face 12, in which the head 13 of the femoral part pivots and an external face 14, designed to be fixed in the cotyla of the hip. An axial fixing pin 5, having a diameter of 14.5 mm, also ensures a correct positioning and holding in place during the re-ossification period. One or several other fixing pins, whose axes are parallel to that of the first, can be added to make the holding in place during the re-ossification period easier, as disclosed in U.S. Pat. No. 3,871,031.

A first series of three grooves 16 of the part, having a width of 1.2 mm and a depth of 1 mm, is machined between cylinders parallel to the axis of the hemi-sphere. The ribs separating the grooves have a width of 1.5 mm. A second series of four grooves 17 of the part, having a width and a depth which are respectively equal to the preceding ones, is machined between cones of generating lines at 45° to the axis of the part and whose apexes are situated on the axis of the part, for example in the vicinity of the centre of the enveloping hemi-sphere. A third series of five grooves 18 is machined between planes perpendicular to the axis of the part, as had been disclosed in the U.S. Pat. No. 3,871,031. That network of grooves can, to great advantage, be completed by an orthogonal network of grooves machined along latitudinal lines of the hemi-sphere, not shown, similar to the grooves 3 in FIG. 1. The fixing pin is also provided with grooves 9 arranged between planes perpendicular to the common axis.

The surface of the hemi-sphere, without any fixing pin and without grooves, would measure about 35 squ.cm. An acetabular part provided with nine grooves machined perpendicular to the axis, such as that in FIG. 1, would have a developed surface of 40 squ.cm. The part provided with the machined grooves as described hereinabove with reference to FIG. 2 has a developed surface of 44 squ.cm. This arrangement makes it possible to increase the number of grooves for a given surface of the enveloping hemi-sphere and hence to obtain a better fixing of the acetabular part when the new growing of the bone has taken place.

It will be understood that various modifications can be made to the part which has just been described, although the latter is a preferred embodiment, without going beyond the scope of the invention. More particularly, the dimensions and profiles of the grooves and ribs can be modified, as can the number of groups of grooves whose sections are set in the same direction and the number of grooves in each group. Likewise, the diameter of the fixing pin can be modified.

What is claimed is:

1. In a prosthesis device intended for replacing a bone joint and comprising two parts, one part for connecting to one bone and the other part for connecting to another bone, said one part having a spherical internal surface and a spherical external surface, said one part having an axis lying along a diameter of the sphere defining said spherical external surface, said spherical external surface defining a plurality of grooves arranged in planes perpendicular to said axis, said another part having a spherical external surface for mating with the spherical internal surface of said one part, the improvement wherein the groove walls of at least some of the grooves in the spherical external surface of said one part lie in cones, the apexes of said cones intersecting said axis.

2. The device of claim 1 wherein said spherical internal surface is shaped in the form of a section of a sphere, said sphere section defining a circle, said axis being perpendicular to the plane of said circle.

3. The device of claim 2 wherein said sphere section is a hemisphere.

4. The device of claim 2 wherein the apexes of said cones intersect said axis at the approximate center of the sphere defining said sphere section.

5. The device of claim 2 wherein the generatrixes of said cones form angles of about 45° with said axis.

6. The device of claim 2 wherein the spherical external surface of said one part, the spherical internal surface of said one part and the spherical external surface of said other part are formed from sintered alumina.

7. The device of claim 2 wherein the groove walls of some of said grooves are parallel to said axis and further wherein the groove walls of some of said grooves are perpendicular to said axis.

8. The device of claim 7 wherein said grooves are arranged in groups, a first group of grooves having groove walls parallel to said axis, a second group of grooves adjacent said first group of grooves having groove walls lying on said cones and a third group of grooves next to said second group having groove walls perpendicular to said axis.

9. The device of claim 8 wherein said axis intersects the spherical external surface of said one part at a point of intersection, said third group of grooves being remote from said point of intersection, said first group of grooves being adjacent to said point of intersection and said second set of grooves being intermediate said first and third groups.

10. The device of claim 9 wherein said one part defines a projection integral with said spherical external surface.

11. The device of claim 10 wherein said projection defines a plurality of grooves.

12. The device of claim 2 wherein the groove walls of each groove lying on said cones are parallel.

13. In a prosthesis device intended for replacing a bone joint comprising two parts, one part for connecting to one bone and the other part for connecting to another bone, said one part having a spherical internal surface, said another part having a mating spherical external surface, the spherical internal surface of said one part being shaped in the form of a section of a sphere, said section terminating in a circular base, said one part having a convex external surface defining a plurality of grooves arranged in planes parallel to the plane of the circle defining said circular base, the improvement wherein the groove walls of at least some of the grooves in said external convex surface lie in cones, the apexes of said cones intersecting a line passing through the center of the sphere defining the spherical internal surface of said one part, said line being perpendicular to said plane.

14. The device of claim 13 wherein the generatrixes of said cones form angles of about 45° with said axis.

15. The device of claim 14 wherein the groove walls of each groove lying on said cones are parallel.

* * * * *